United States Patent [19]

Yoshida et al.

[11] Patent Number: 4,916,074
[45] Date of Patent: Apr. 10, 1990

[54] PROCESS FOR PRODUCING OPTICALLY ACTIVE COMPOUNDS

[75] Inventors: Naoyuki Yoshida; Hiroshi Morita, both of Yokohama, Japan

[73] Assignee: Chisso Corporation, Osaka, Japan

[21] Appl. No.: 113,764

[22] Filed: Oct. 28, 1987

[30] Foreign Application Priority Data

Oct. 30, 1986 [JP] Japan .................................. 61-256952
Nov. 7, 1986 [JP] Japan .................................. 61-263837

[51] Int. Cl.$^4$ .............................................. C12P 41/00
[52] U.S. Cl. .................................... 435/280; 435/134; 435/135
[58] Field of Search ........................ 435/135, 134, 280

[56] References Cited

U.S. PATENT DOCUMENTS 4,451,565  5/1984  Gatfield et al. ...................... 435/135

OTHER PUBLICATIONS

Cambou et al.-Annals of N.Y. Acad. Science, vol. 434 (1984), pp. 219-222.
Cambou et al.-J.A.C.S., vol. 106 (1984), pp. 2687-2692.
Kirchner et al.-J.A.C.S., vol. 107 (1985), pp. 7072-7076.
Derwent Abstract-Japanese Patent-63-123399 (May 27, 1988).

Primary Examiner—Sam Rosen
Attorney, Agent, or Firm—Wenderoth, Lind & Ponack

[57] ABSTRACT

The present invention provides a process for producing optically active compounds by a biochemical method in which specific compounds having hydroxyl groups are reacted with esters in the presence of enzymes. The compounds have the following general formula.

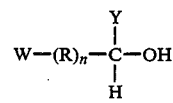

wherein Y is selected from the group consisting halogen atoms, alkyl groups having 1-3 carbon atoms, cyano groups, and trifluoromethyl groups, W is selected from the group consisting substituted phenyl groups, and halogen atoms, cyano, trifluoromethyl and amino groups and alkylamino and alkyloxycarbonyl groups in which alkyl groups have 1-20 carbon atoms, R is methylene and n is 0 or 1.

The enzymes having ability of transesterification reaction is preferably lipase, lipoprotein lipase, esterase and so on, and micro-organisms can be used in the above process.

6 Claims, No Drawings

PROCESS FOR PRODUCING OPTICALLY ACTIVE COMPOUNDS

BACKGROUND OF THE INVENTION

1. Fields of the Invention

The present invention relates to a process for producing optically active compounds by a biochemical method in which specific compounds having hydroxyl groups are reacted with esters in the presence of enzymes.

2. Description of the Prior Art

Optically active compounds represented by the general formula (I) are useful chemical compounds as starting materials of medical supplies, agricultural chemicals and the like. However, the compounds have optical isomers, so that they do not sufficiently exhibit their characteristics in many cases unless either an R- or S-alcohol is purely contained.

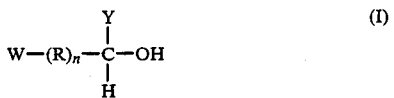

wherein Y is selected from the group consisting halogen atoms, alkyl groups having 1-3 carbon atoms, cyano groups, and trifluoromethyl groups, W is selected from the group consisting the following groups:

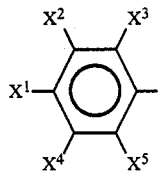

wherein $X^1$, $X^2$, $X^3$, $X^4$ and $X^5$ are selected from the group consisting hydrogen and halogen atoms, cyano, trifluoromethyl, amino, alkylamino, aryloxy, and the following goups:

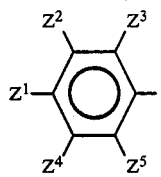

and alkyl and alkoxy groups having 1-20 carbon atoms, $Z^1$, $Z^2$, $Z^3$, $Z^4$ and $Z^5$ are selected from the group consisting hydrogen and halogen atoms, cyano, trifuluoromethyl, and amino groups and alkylamino, alkyl and alkoxy groups having 1-20 carbon atoms, and halogen atoms, cyano, trifluoromethyl and amino groups and alkylamino and alkyloxycarbonyl groups in which alkyl groups have 1-20 carbon atoms, R is methylene and n is 0 or 1.

For the above reason, in order to an obtain optically active substance, it is needed to optically resolve a racemate which is obtained by a common method of synthetic chemical technique, to conduct asymmetric synthesis or to convert from an optically active starting material by a stereochemical synthetic method. In many cases, the process is troublesome and disadvantageous industrially.

Accordingly, it is desired to develop a technique for obtaining optically active compounds by an industrially advantageous method.

As a known biochmical technique, for example, there is a method described in Japanese Publication of Unexamined Patent Application No. 59-205989 in which a racemic ester is hydrolyzed with a lipase and an desired alcohol is obtained. In this case, the racemic ester is often insoluble in water, so that it is necessary to emulsify or stir vigorously by using a large quantity of water. Klibanov et al. reported a method in which enzyme powder was directly added into a reaction system (J. Am. Chem. Soc., 107, 7072 (1985). In this case, esters for transesterification are extremely limited and 2,2,2-trichloroethyl butyrate is used as the ester.

Furthermore, it is essential to use an organic solvent, such as heptane or ether which has many problems when it is used industrially.

The inventors of the present invention conducted research for resolving the above problems and obtaining a process for producing optically active compounds represented by the above general formula (I) by an advantageous industrial method and then found that racemic compounds of raw materials are efficiently resolved to optically active compounds and their antipodes, namely optically active esters, by a biochemical transesterification reaction.

SUMMERY OF THE INVENTION

Namely, the present invention provides a process for producing an optically active compound and its ester that comprises using an enzyme having the ability to conduct preferentially a transesterification reaction with a corresponding ester and an (R,S)-alcohol represented by the above general formula (I), reacting the (R,S)-alcohol and the corresponding ester to conduct the transesterification reaction under substantially anhydrous conditions and resolving the resulting compound to obtain an optically active compound which contains richly either an R- or S-compound and its ester.

According to the method of the present invention in comparison with conventional methods, the reaction is conducted under anhydrous conditions. This method needs not use a small amount of water or a lower alcohol instead of the water, so that the enzyme is stably kept in organic solvent and is easily separated after the reaction and reused. Furthermore, as the method of the present invention is kept free from contamination by microorganisms, there is no necessity for preparing special equipment, antiseptics, sterilization treatment, etc. It is possible to conduct the reaction in an open system. Further, the reaction may be conducted in the same or smaller quantity of solvent in comparison with common organic synthetic reactions in high substrate concentration.

The following description illustrates this invention more specifically.

In this invention, the (R,S)-alcohols of the starting materials are compounds which are available and can be synthesized.

It is also enough to use esters, preferably triglycerides, which are commercially available without any difficulty. Triacetin, tripropionin, tributyrin, tristearin, trilaurin, trimyristin, triolein etc. can be exemplified as the triglycerides. As the other esters, methyl propionate, ethyl butyrate, ethyl stearate, trichloroethyl laurate, butyl laurate, ethylene glycol diacetate, etc., can be used.

As the enzyme which is used in this invention, lipase, lipoprotein lipase, esterase, etc. is preferable. If the enzyme has ability of transesterification reaction preferentially between the R- or S-alcohol and the ester when the enzyme is used with the (R,S)-alcohol, the enzyme can be used regardless its class. The following table shows commercially available enzyme that can be used in this reaction.

TABLE

| Trade name | Origin | Seller or Maker |
|---|---|---|
| Lipase AP | Aspergillus niger | Amano Pharmaceutical Co. Ltd |
| Lipase M | Mucor javanicus | Amano Pharmaceutical Co. Ltd |
| Lipase P | Pseudomonas fluorescens | Amano Pharmaceutical Co. Ltd |
| Lipase CES | Pseudomonas sp | Amano Pharmaceutical Co. Ltd |
| Lipase CE | Humicola lanuginosa | Amano Pharmaceutical Co. Ltd |
| Lipase F-AP | Rhizopus javanicus | Amano Pharmaceutical Co. Ltd |
| Lipase II | Porcine Pancreas | Sigma Chemical Co. |
| Lipase VIII | Geotrichum Candidum | Sigma Chemical Co. |
| Lipase X | Rhizopus delamar | Sigma Chemical Co. |
| Lipase | Chromobacterium Viscosum | Toyo Jozo Co., Ltd. |
| Palatase A | Aspergillus niger | Novo Industi A/S |
| Lipase | Rhizopus niveus | Nagase Biochemicals, Ltd. |

In addition to these enzymes, microorganisms which produce the enzymes having the above ability can be used regardless their species and genus. As such microorganisms, Arthrobacter genus, Acromobacter genus, Alcaliqenes genus, Aspergillus genus, Chromobacterium genus, Candida genus, Mucor genus, Pseudomonas genus, Rhizopus genus etc. can be exemplified.

In the practice of the present invention, (R,S)-compounds and esters such as triglycerides can be used without any particular treatments.

The reaction is conducted by mixing an (R,S)-compound with an ester, preferably a triglyceride, if necessary, adding an organic solvent such as heptane or toluene when the ester is slightly soluble in the compound, and contacting efficiently the mixture with an enzyme. Its reaction temperature is suitably 20°–70° C. and especially preferably 30°–45° C. Its reaction time is broadly 5–2000 hours. It is possible to shorten the reaction time by elevating the reaction temperature or lowering the substrate concentration.

The (R,S)-compound which is a substrate and the ester are mixed in the ratio 1:0.5–1:5 by mole, and preferably 1:1.1–1:2 by mole.

After the transesterification reaction, the enzyme can be removed by common filter operation and used again as it is. The filtrate can be separated into an optically active compound and an ester, respectively, by distillation or column chromatography. The obtained ester is hydrolyzed in an alkali or acid solution to derive the optically active compound which is an antipode of the above compound.

By the above described process, the optically active R- and S-compound can be obtained.

The effects of this invention are as follows.

(1) Unnecessary hydrolysis of esters is scarcely occurs because the transesterification reaction is substantially conducted under anhydrous conditions.

(2) The enzyme can be easily recovered and reused.

(3) No special equipment and materials are used because the reaction can be conducted under the conditions of relatively low temperatures and an open system.

(4) Optically active substances having high purity are obtained by a one step reaction.

(5) In spite of biochemical reaction, substrate concentration can be increased and big reaction vessels are unnecessary, because a buffer solution and the like are not required in the reaction.

DESCRIPTION OF PREFERRED EMBODIMENTS

The following examples illustrate this invention more specifically, but these will not always be precise in practical applications.

EXAMPLE 1

Twenty grams of enzyme (produced by Amano pharmaceutical Co. Ltd., lipase "Amano P"), 48.9 g (0.4 mol) of (R,S)-α-phenylethyl alcohol and 133.0 g (0.44 mol) of tributyrin were charged into three-necked flask and reacted with stirring for nine days at 35° C. After the reaction was stopped, the enzyme was removed by filtration and the desired compounds were isolated from the filtrate by distillation under reduced pressure. As the result, 28.4 g of S-(−)-α-phenylethyl alcohol (yield: 58%, $[\alpha]D = -35.1°$ (neat)) was obtained at the boiling point of 52°–62° C./3 mmHg, and R-(+)-1-phenylethyl butyrate was obtained. By hydrolysis of the ester, 18.3 g of R-(+)-α-phenylethyl alcohol (yield: 38%, $[\alpha]_D = +41.2°$ (neat)) was obtained.

The obtained compounds were identified by structure analysis with NMR.

EXAMPLE 2

Ten grams of enzyme (produced by Amano pharmaceutical Co. Ltd., lipase "Amano P"), 9.0g (35 mmol) of (R,S)-4-(1-hydroxyethyl)-4'-pentylbiphenyl and 15.9 g (52.5 mmol) of tributyrin were dissolved in the mixed solvent of 100 ml of heptane and 50 ml of toluene and the mixture was charged into three-necked flask and stirred for 15 days at 35° C. After the reaction was stopped, the enzyme was removed by filtration and the filtrate was concentrated. The residue was chromatographed over silica gel, and the desired compounds were isolated. As the result, 2.6 g of (−)-4-(1-hydroxyethyl)-4'-pentylbiphenyl (yield: 29%, $[\alpha]_D = -25.0°$ (c1.0, MeOH) and 2.5 g of (+)-4-(1-butyryloxyethyl)-4'-pentylbiphenyl (yield: 22%, $[\alpha]_D = +96.4°$ (c1.0, MeOH) were obtained.

EXAMPLE 3

Using the same method as in Example 2, (R,S)-4-octyloxy-4'-(1-hydroxyethyl)biphenyl was reacted with tributyrin. As the result, (−)-4-octyloxy-4'-(1-hydroxyethyl)biphenyl ($[\alpha]_D = -27.0°$ (c1.0, CHCl$_3$)) and (+)-4-(1-butyryloxyethyl)-4'-octyloxybiphenyl ($[\alpha]_D = +94.0°$ (c0.1, MeOH) were obtained.

EXAMPLE 4

Using the same method as in Example 1, (R,S)-1-(4-heptyloxyphenyl) ethanol was used as a starting material, and reacted with tributyrin. As the result, (−)-1-(4-heptyloxyphenyl)ethanol (yield: 48%, $[\alpha]_D = -14.4°$ (c1.0, MeOH)) and (+)-1-(4-heptyloxyphenyl)ethyl butyrate were obtained. Further, this (+)-1-(4-heptyloxyphenyl)ethyl butyrate was hydrolyzed, and (+)-1-(4-heptyloxyphenyl)ethanol (yield: 30%, $[\alpha]_D = +24.9°$ (c1.0, MeOH)) was obtained.

EXAMPLE 5

Using the same method as in Example 1, (R,S)-1-phenyl-2-propanol and tributyrin were reacted to obtain S-(')-1-phenyl-2-propanol ($[\alpha]_D = +23.7°$ (neat)) and R-(−)-1-phenyl-2-propyl butyrate. Further, the obtained butyrate was hydrolyzed, and R-(−)-1-phenyl-2-propanol ($[\alpha]_D = -26.2°$ (neat)) was obtained.

EXAMPLE 6

Using the same method as in Example 1, (R,S)-1-(2-bromophenyl)ethanol and tributyrin were reacted to obtain S-(+)-1-(2-bromophenyl)ethanol (68% ee) and R-(−)-1-(2-bromophenyl)ethyl butyrate. Further, the obtained butyrate was hydrolyzed, and R-(−)-1-(2-bromophenyl)ethanol (95%ee). Their optical purities were checked with HPLC by using CHIRAL CEL OB made by DAISEL Co. Ltd. as a column for optical resolution. The eluent was hexane/isopropanol (9:1).

EXAMPLE 7

Sixty-six grams (0.5 mol) of racemic ethyl β-hydroxybutyrate, 166.3 g (0.6 mol) of tributyrin, and 80 g of lipase "Amano P" were mixed and reacted with stirring for ten days at 35° C. After the lipase was removed by filtration, the reaction was stopped.

The filtrate was distilled under vacuum. 14.7 g of S-(+)-ethyl β-hydroxybutyrate (yield: 44.5%) ($[\alpha]_D = +17.3°$ (c1.0, CHCl₃)) and 16.3 g of R-(−)-ethyl β-butyryloxybutyrate (yield: 32%) ($[\alpha]_D = -0.3°$ (c1.0,CHCl₃)) were separated, respectively.

EXAMPLE 8

Using the same method as described in Example 1, 37.6 g (0.235 mol) of racemic tert-butyl β-hydroxybutyrate was resolved. 7.8 g of S-(+)-tert-butyl β-hydroxybutyrate (yield: 41%) ($[\alpha]_D = +28.2°$ (c1.0, CHCl₃)) and 16.2 g of R-(−)-tert-butyl β-butyryloxybutyrate (yield: 60%) ($[\alpha]_D = -0.07°$ (neat, 1 cm cell)) were separated, respectively.

Further, the obtained R-(−)-tert-butyl β-butyryloxybutyrate was hydrolyzed, and R-(−)-tert-butyl β-hydroxybutyrate ($[\alpha]_D = -33.6°$ (c1.0, CHCl₃), 95%ee) was obtained. The obtained butyrate was reduced to 1,3-butanediol. The diol was acetylated. The optical purities of the obtained 1,3-diacetyloxybutane was checked with HPLC by using CHIRAL CEL OB.

We claim:

1. A process for the production of an optically active ester of an alcohol which comprises reacting a triglyceride with an (R,S)-alcohol of the formula

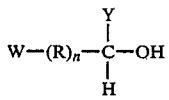

wherein
Y is alkyl of 1-3 carbon atoms,
W is a member selected from the group consisting of
(1)

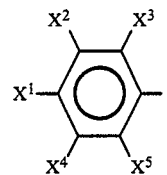

wherein $X^1$, $X^2$, $X^3$, $X^4$ and $X^5$ are hydrogen, halogen, alkyl of 1-20 carbon atoms, alkoxy of 1-20 carbon atoms, or a group of the formula

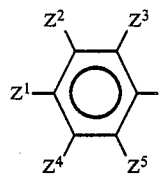

wherein $Z^1$, $Z^2$, $Z^3$, $Z^4$ and $Z^5$ are hydrogen, halogen, alkyl of 1-20 carbon atoms or alkoxy of 1-20 carbon atoms, and (2) alkyloxycarbonyl in which the alkyl moiety is of 1-20 carbon atoms,
R is methylene, and
n is 1,
under substantially anhydrous conditions and in the presence of an enzyme obtained from a Pseudomonas species and having the ability to preferentially conduct a transesterification reaction between the triglyceride and the (R,S)-alcohol to effect the transesterification reaction and obtaining the corresponding R- or S-ester of the alcohol.

2. A process according to claim 1 wherein the triglyceride is tributyrin.

3. A process according to claim 1 wherein Y is methyl.

4. A process for the production of an optically active alcohol which comprises reacting a triglyceride with an (R,S)-alcohol of the formula

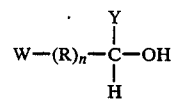

wherein
Y is alkyl of 1-3 carbon atoms,
W is a member selected from the group consisting of
(1)

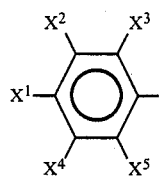

wherein $X^1$, $X^2$, $X^3$, $X^4$ and $X^5$ are hydrogen, halogen, alkyl of 1-20 carbon atoms, alkoxy of 1-20 carbon atoms, or a group of the formula

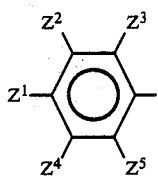

wherein $Z^1$, $Z^2$, $Z^3$, $Z^4$ and $Z^5$ are hydrogen, halogen, alkyl of 1–20 carbon atoms or alkoxy of 1–20 carbon atoms, and (2) alkyloxycarbonyl in which the alkyl moiety is of 1–20 carbon atoms, R is methylene, and n is 1, under substantially anhydrous conditions and in the presence of an enzyme obtained from a Pseudomonas species and having the ability of preferentially conduct a transesterification reaction between the triglyceride and the (R,S)-alcohol to effect the transesterification reaction obtaining the corresponding R- or S-ester of the alcohol and hydrolyzing the ester to the corresponding R- or S- alcohol.

5. A process according to claim 4 wherein the triglyceride is tributyrin.

6. A process according to claim 4 wherein Y is methyl.

* * * * *